(12) United States Patent
Allard et al.

(10) Patent No.: US 11,505,382 B2
(45) Date of Patent: Nov. 22, 2022

(54) PACKAGING SYSTEM WITH SPRING-LOADED REMOVAL

(71) Applicant: Prospect Life Sciences, Inc., Westminster, CO (US)

(72) Inventors: Randall Allard, Golden, CO (US); Jason Morton, Golden, CO (US); Polly Allard, Golden, CO (US); Tom McLeer, Laguna Niguel, CA (US)

(73) Assignee: Prospect Life Sciences, Inc., Westminster, CO (US)

( * ) Notice: Subject to any disclaimer, the term of this patent is extended or adjusted under 35 U.S.C. 154(b) by 0 days.

(21) Appl. No.: 17/443,643

(22) Filed: Jul. 27, 2021

(65) Prior Publication Data

US 2022/0024664 A1   Jan. 27, 2022

Related U.S. Application Data

(60) Provisional application No. 63/056,845, filed on Jul. 27, 2020.

(51) Int. Cl.
*B65D 77/04* (2006.01)
*B65D 75/58* (2006.01)
*B65B 5/04* (2006.01)
*A61B 50/33* (2016.01)
*B65D 75/32* (2006.01)
*A61B 50/00* (2016.01)

(52) U.S. Cl.
CPC .............. *B65D 75/58* (2013.01); *A61B 50/33* (2016.02); *B65B 5/04* (2013.01); *B65D 75/326* (2013.01); *B65D 77/0453* (2013.01); *A61B 2050/0065* (2016.02)

(58) Field of Classification Search
CPC .. B65D 75/58; B65D 75/326; B65D 77/0453; B65D 77/046; A61B 50/33; A61B 50/30; A61B 2050/0065
USPC ........................................ 206/438, 363, 370
See application file for complete search history.

(56) References Cited

U.S. PATENT DOCUMENTS

| | | | |
|---|---|---|---|
| 4,750,619 A * | 6/1988 | Cohen .................. | B65D 81/127 206/828 |
| 5,148,920 A * | 9/1992 | Walker .................. | A61F 2/0095 206/592 |
| 7,234,597 B2 | 6/2007 | Rowe et al. | |
| 8,186,511 B2 * | 5/2012 | Timm ..................... | A61P 35/00 206/572 |

(Continued)

*Primary Examiner* — Jacob K Ackun
(74) *Attorney, Agent, or Firm* — BrainSpark Associates, LLC

(57) ABSTRACT

A multi-unit packing system includes a packaging tray assembly supporting a medical device or product. The packaging tray assembly includes a tray that holds the medical product within a spring-loaded card. The spring-loaded card being disposed within the inner container of the tray. The spring-loaded card including a one or more openings that are positioned to maintain the medical product in a defined orientation while preventing the inadvertent movement of the medical product. The spring-loaded card comprises elastic properties to allow it to be elastically compressed when the barrier is sealed to the tray, and uncompressed when the barrier is peeled away from the tray, allowing a portion of the spring-loaded card to extend beyond a surface of the tray to provide easier access, removal and transfer of the sterile medical product within the sterile field.

20 Claims, 11 Drawing Sheets

(56) References Cited

U.S. PATENT DOCUMENTS

| | | | |
|---|---|---|---|
| 2006/0282045 A1 | 12/2006 | Wilkinson et al. | |
| 2007/0034538 A1* | 2/2007 | Landis | A61F 2/0095 206/363 |
| 2008/0063760 A1* | 3/2008 | Raymond | B65D 81/3453 426/531 |
| 2008/0230422 A1* | 9/2008 | Pleil | A61B 90/98 606/280 |
| 2015/0250551 A1* | 9/2015 | Ries | A61B 90/90 206/438 |

* cited by examiner

PACKAGING SYSTEM WITH SPRING-LOADED REMOVAL

TECHNICAL FIELD

This invention relates to methods, devices, and systems for a multi-unit packaging system with improved removal, access and transfer of sterilized medical products. More specifically, multi-unit packaging system includes a plurality of packaging tray assemblies that includes a spring-loaded card with a leading edge or tab that extends beyond a top surface of the tray or flange for improved removal, access and transfer of sterilized medical products.

BACKGROUND OF THE INVENTION

Traditionally, medical packaging tray assemblies has provided trays or die-cut cards with different features, such as edge reliefs, finger tabs, pull tabs, that are made out of a material that are folded flat and stay flat or planar with the tray surface. Such traditional features are not effective with the access, removal and transfer of sterilized medical products.

BRIEF SUMMARY OF THE INVENTION

In one exemplary embodiment, the method of easier access to a medical product comprising the steps of: providing a tray with an inner container and a flange, the flange surrounding the perimeter of the inner container, the flange having a top surface; creating a spring loaded card with an original configuration, the spring loaded card comprising a material, a body and a leading edge; disposing a portion of a medical product within a portion of the spring loaded card and placing the spring loaded card with the original configuration within the inner container of the tray; compressing the spring-loaded card within the inner container by coupling a barrier to the top surface of the flange to create a compressed configuration to enable the storage of potential energy; and peeling the barrier away from the top surface of the flange to enable the release of potential energy allowing the spring loaded card return to its original configuration; and accessing a portion of the spring-loaded card in its original configuration by having the portion of the spring loaded card extending beyond the top surface of the flange for easier access and removal of the medical product.

In another exemplary embodiment, the multi-unit packaging system comprises a packaging tray assembly, the packaging tray assembly comprises a tray, a spring-loaded card and a barrier, the spring-loaded card is disposed within the tray, the spring-loaded card comprising a leading edge and a body, at least a portion of the spring-loaded card being movable from a compressed state after the barrier is coupled onto a top surface of the tray that enables the potential energy to be stored to an uncompressed state after the barrier is removed from the top surface of the tray that enables the potential energy to be released and allowing a portion of the spring-loaded card to extend beyond the top surface of the tray; and a multi-unit compartment carrier, the multi-unit compartment carrier comprising at least one compartment that is sized and configured to receive the packaging tray assembly. The multi-unit packaging system may further comprise a medical device.

In another exemplary embodiment, the multi-unit packaging system comprises a packaging tray assembly, the packaging tray assembly comprises a tray, a spring-loaded card and a barrier, the spring-loaded card is disposed within the tray, the spring-loaded card comprising a leading edge and a body, the leading edge being movable from a compressed state after the barrier is coupled onto a top surface of the tray that enables the potential energy to be stored to an uncompressed state when the barrier is removed that enables the potential energy to be released and allowing the leading edge of the spring-loaded card to extend beyond the top surface of the tray; and a multi-unit compartment carrier, the multi-unit compartment carrier comprising at least one compartment that is sized and configured to receive the packaging tray assembly. The multi-unit packaging system may further comprise a medical device.

In another exemplary embodiment, a multi-unit packaging system comprises a a packaging tray assembly, the packaging tray assembly comprises a tray, a spring-loaded card and a barrier, the spring-loaded card being sized and configured to be disposed within the tray, the spring-loaded card comprising a material and an original configuration, the spring-loaded card being elastically deformed to a compressed configuration when compressed by the barrier being coupled to a top surface of the tray and returned to its original configuration when uncompressed after the barrier is removed from the top surface of the tray; and a multi-unit compartment carrier, the multi-unit compartment carrier comprising at least one compartment that is sized and configured to receive the packaging tray assembly. The multi-unit packaging system may further comprise a medical device.

In another exemplary embodiment, the sterile packaging tray assembly comprises a tray, the tray comprising an inner container and a flange, the flange surrounds the perimeter of the inner container, the flange having a top surface; a spring-loaded card, the spring-loaded card being sized and configured to be disposed within the inner container, the spring-loaded card comprising a body and a leading edge, at least a portion of the spring-loaded card being movable from a compressed state after the barrier is coupled onto a top surface of the flange that enables the potential energy to be stored to an uncompressed state after the barrier is removed from the top surface of the flange that enables the potential energy to be released and allowing the at least a portion of the spring-loaded card to extend beyond the top surface of the flange. The packaging tray assembly may further comprise a medical device.

In another exemplary embodiment, the sterile packaging tray comprises a tray, the tray comprising an inner container and a flange, the flange surrounds the perimeter of the inner container, the flange having a top surface; a spring-loaded card, the spring-loaded card being sized and configured to be disposed within the inner container, the spring-loaded card comprising a body and a leading edge, the leading edge being movable from a compressed state that enables the potential energy to be stored to an uncompressed state after the barrier is removed from the top surface of the flange that enables the potential energy to be released and the leading edge of the spring-loaded card to extend beyond the top surface of the flange; and a barrier, the barrier being disposed onto the top surface of the flange. The packaging tray assembly may further comprise a medical device.

In another exemplary embodiment, the sterile packaging tray assembly comprises a tray, the tray comprising an inner container and a flange, the flange surrounds the perimeter of the inner container, the flange having a top surface; and a spring-loaded card, the spring-loaded card being sized and configured to be disposed within the inner container, the spring-loaded card comprising a material and an original configuration, at least a portion of the spring-loaded card being elastically deformed when compressed within the tray after a barrier is disposed on the top surface of the flange to create a compressed configuration and the at least a portion of the spring-loaded card is returned to the original configuration when uncompressed after the barrier is removed from the top surface of the flange. The packaging tray assembly may further comprise a medical device.

In another exemplary embodiment, the sterile packaging tray assembly comprises a tray, the tray comprising an inner container and a flange, the flange surrounds the perimeter of the inner container, the flange having a top surface; and a spring-loaded card, the spring-loaded card being sized and configured to be disposed within the inner container, the spring-loaded card comprising a body, a leading edge, and a material, the leading edge of the spring-loaded card being elastically deformed when compressed within the tray after a barrier is disposed on the top surface of the flange to create a compressed configuration and the at least a portion of the spring-loaded card is returned to an original configuration when uncompressed after the barrier is removed from the top surface of the flange. The packaging tray assembly may further comprise a medical device.

In another exemplary embodiment, the sterile packaging tray assembly comprises a first tray and a second tray, the first tray comprising a first inner container and a first flange, the first flange surrounds the perimeter of the first inner container, the first flange having a first top surface, the second tray comprising a second inner container and a second flange, the second flange surrounds the perimeter of the second inner container, the second flange having a second top surface, the second tray disposed within the first inner container of the first tray; a barrier; a spring-loaded card, the spring-loaded card being sized and configured to be disposed within the second inner container, the spring-loaded card comprising a body and a leading edge, the body including at least one wall that extends perpendicular or substantially perpendicular to the longitudinal axis of a medical product, at least a portion of the spring-loaded card being movable from a compressed state after the barrier is coupled to first and second top surface of the first and second tray that enables the potential energy to be stored to an uncompressed state after the barrier is removed from the first and second top surface of the first and second tray that enables the potential energy to be released and allowing at least a portion of the spring-loaded card to extend beyond the top surface of the first flange.

DETAILED DESCRIPTION OF THE INVENTION

Multi-Unit Packaging System and Packaging Tray Assembly

The multi-unit packaging system provides improved access, removal, and transfer of medical products within a sterile field. The multi-unit packaging system comprises a multi-compartment carrier and a packaging tray assembly. The packaging tray assembly comes equipped with a tray, a barrier and spring-loaded card having elastic material properties. A medical product is disposed within the spring-loaded card, and the spring-loaded card is disposed within the tray. The spring-loaded card provides the "spring" or "pop-up" mechanism or easier access to the medical product v, as well as provides stability and protection within the tray. The stability and protection are achieved during the compression of the spring-loaded card within the tray to prevent tumultuous movement, axial translation and/or prevent abrasion or puncture of the barrier. The barrier is heat sealed over the tray and this action compresses the spring-loaded card with the medical product to enable the storage of potential energy. When the medical staff begins preparation of the surgical tools, equipment and implants within the sterile field, the medical staff will retrieve a packaging tray assembly from the multi-compartment carrier and begin to peel the barrier from the tray. The opening of the barrier releases the stored potential energy of the spring-loaded card transferring to kinetic energy and allowing a portion of the spring-loaded card to extend beyond the surface of the tray for easy access, removal, and transfer of the sterile medical product. The medical product may comprise a screw.

Figure 1A:
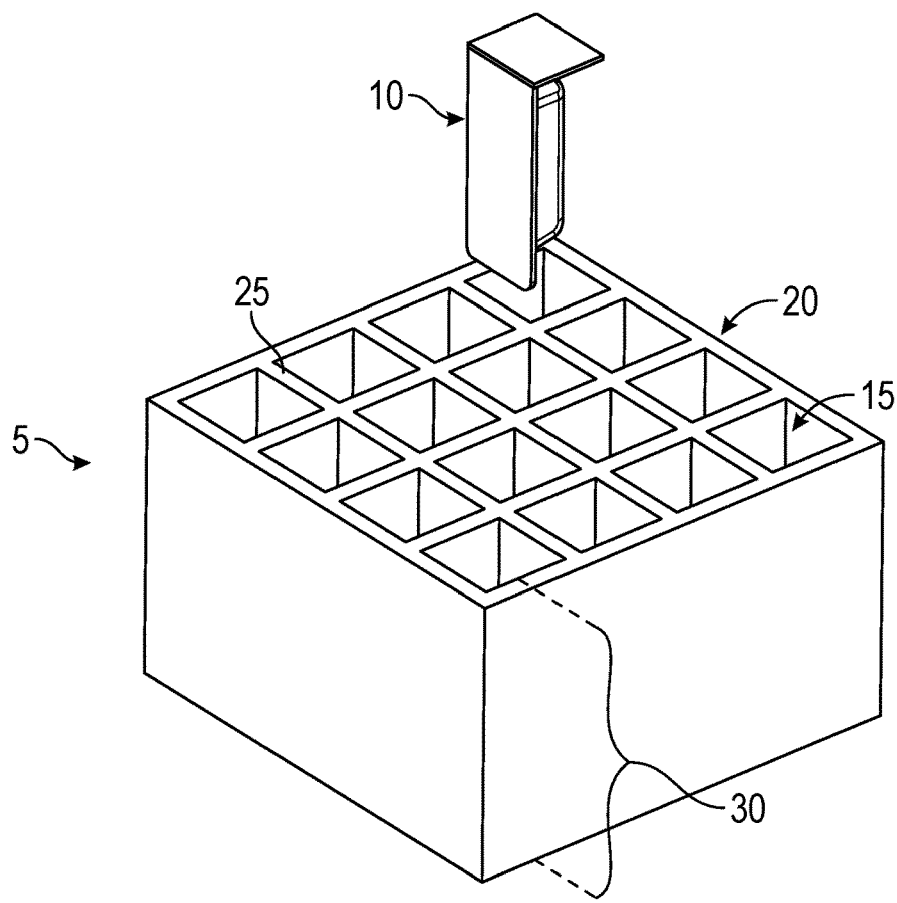
FIGS. 1A-1D depicts various views of one embodiment of a multi-unit packaging system.
Figure 1B:
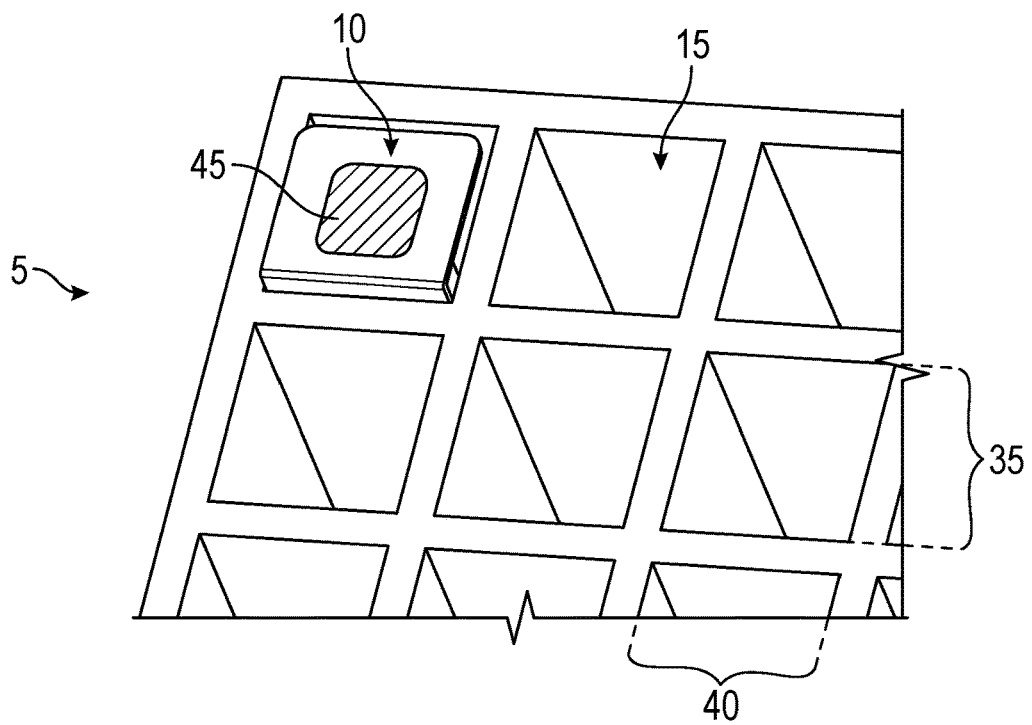
Figure 1C:
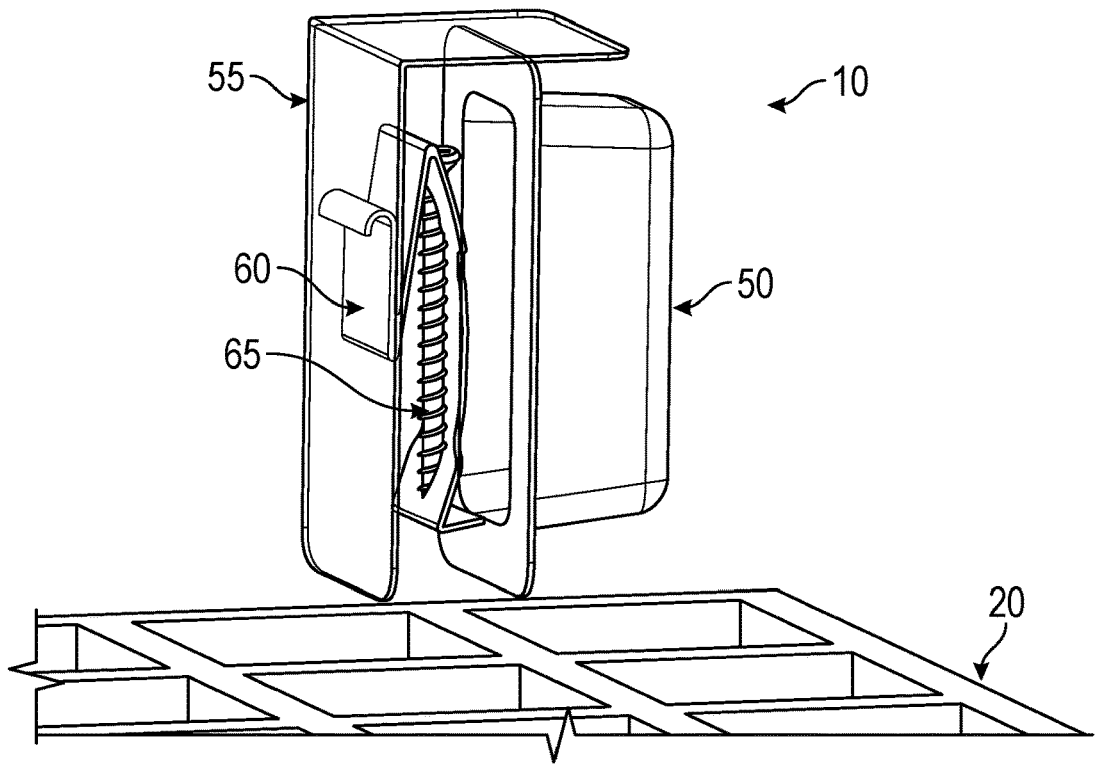
Figure 1D:
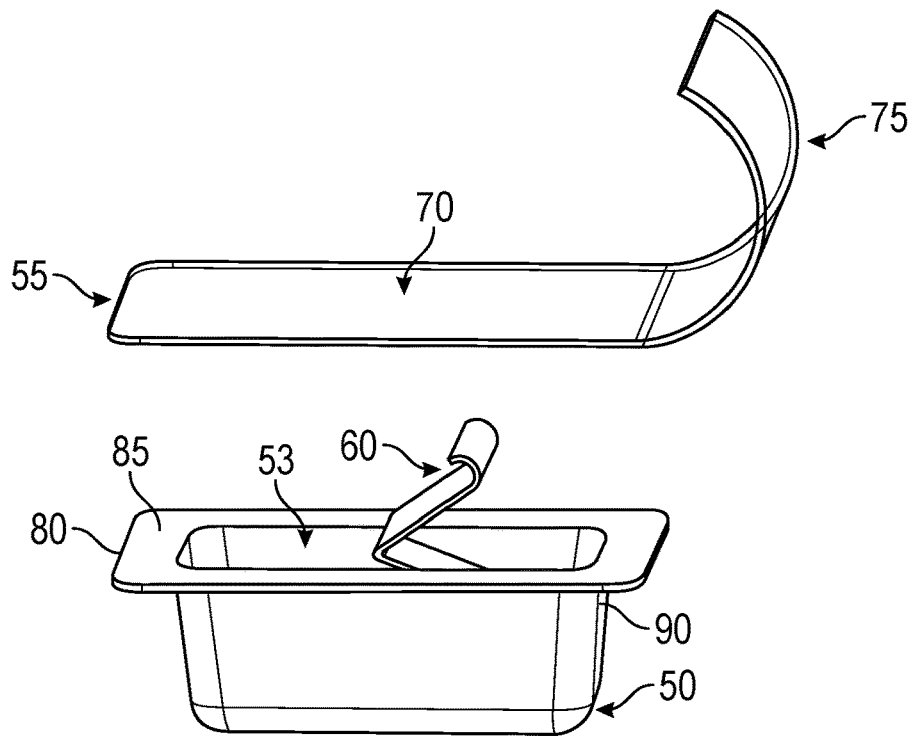

FIGS. 1A-1C depicts various views of one embodiment of a multi-unit packaging system 5. The multi-unit packaging system 5 comprises at least one packaging tray assembly 10 and at least one box 20. The at least one box 20 comprises one or more compartments 15. The one or more compartments 15 are spaced apart and sized and configured to receive at least a portion of the packaging tray assembly 10. Alternatively, the one or more compartments 15 are spaced apart, and sized and configured to receive the entire packaging tray assembly 10. The one or more compartments 15 are arranged in a plurality of rows, each of the plurality of rows are aligned the prior and/or next plurality of rows. Alternatively, the plurality of rows may be offset from the prior and/or the next plurality of rows. The at least one box 20 provides for an improved condensed packaging arrangement for long medical products, such as orthopedic screws.

Each of the one or more compartments 15 may comprise a height 30, a width 35 and a length 40. The height 30 of the one or more compartments 15 may be equal to a height of the packaging assembly tray 10. The height 30 of the one or more compartments may be less than the height of the packaging tray assembly 10. The height 30 of the one or more compartments 15 may be greater than the height of the packaging assembly tray 10. Accordingly, each of the one or more compartments 15 are surrounded by a plurality of walls 25. The plurality of walls 25 are spaced apart and arranged in a plurality of rows and intersected with an additional plurality of walls 25 that are spaced apart.

The box 20 may comprise a top surface. The top surface of the packaging tray assembly 10 is flush with the top surface of the box 20. The top surface of the packaging tray assembly 10 is greater and/or above the top surface of the box 20. The top surface of the packaging tray assembly 10 is less than and/or lower than the top surface of the box 20.

The multi-unit packaging system may further comprise a carrier (not shown). The box 20 may be disposed within the carrier. The box 20 and the carrier may comprise a material. The box material and the carrier material may comprise the same or different materials. The carrier material may comprise a harder or more rigid material than the box material. The box material may comprise a polymer, a foam, a thermoplastic foam, a thermoset foam, and/or any combination thereof. The carrier may comprise a ceramic, metal and/or a polymer. The polymers may be standard polymers known in the art for packaging.

FIGS. 1D, 2A-2B, 3A-3B, 6 and 9A-9B depicts several views of different embodiments of a packaging tray assembly 10, 135, 160, 170. The packaging tray assembly 10, 135, 160, 170 comprises at least one tray 50, 50a, 50b, a tray barrier 55 and a spring-loaded card 60, 145, 175. The sterile packaging tray assembly 10, 135, 160 comprises at least one tray 50, 50a, 50b, the at least one tray 50, 50a, 50b comprising a body 90, an inner container 53 and a flange 80, the flange 80 surrounds the perimeter of the inner container 53, the flange 80 having a top surface 85. The inner container 53 is sized and configured to have a uniform shape. Alternatively, the inner container 53 is sized and configured to have a non-uniform shape. In addition, the inner container 53 is sized and configured to have a tapered shape, where the top end having the largest opening and the bottom end having a thinner or smaller opening. In addition, the inner container 53 being sized and configured to receive at least a portion of a spring-loaded card 60, 145, 175. The inner container 53 being sized and configured to receive the entire spring-loaded card 60, 145, 175. The at least one tray 50, 50a, 50b having a top surface and a bottom surface. The inner container 53 and/or the at least one tray 50, 50a, 50b may be manufactured according to standard methods known in the art.

The at least one tray 50, 50a, 50b comprises a flange 80, the flange 80 surrounds the perimeter of at least one end of the tray 50, 50a, 50b and/or the body 90 of the at least one tray 50, 50a, 50b. Alternatively, the flange 80 surrounds the top surface of the at least one tray 50, 50a, 50b. The flange 80 extends away from the at least one end of the tray 50, 50a, 50b. The flange 80 extends perpendicularly away from the at least one end of the tray 50, 50a, 50b or extends perpendicularly away from the top surface of the tray 50, 50a, 50b. The flange 80 being planar, the flange 80 having a top surface 85, a width and a length.

In another exemplary embodiment, the sterile packaging tray assembly 10, 135, 160, 170 comprises a first tray 50a and a second tray 50b, the first tray 50a comprising a first inner container 53a and a first flange 80a, the first flange 80a surrounds the perimeter of the first inner container 53a, the first flange 80a having a first top surface 85a, the second tray 50b comprising a second inner container 53b and a second flange 80b, the second flange 80b surrounds the perimeter of the second inner container 53b, the second flange 80b having a second top surface 85b, the second tray 50b disposed within the first inner container 53a of the first tray 50a. The top surface 85a of the first flange 80a is flush with the top surface 85b of the second tray 50b. Alternatively, the top surface 85a of the first flange 80a is below and/or above the top surface 85b of the second tray 50b.

The first flange 80a surrounds the perimeter of at least one end of the first tray 50a and the second flange 80b surrounds the perimeter of at least one end of the second tray 50b. Alternatively, the first flange 80a surrounds the top surface of the first tray 50a and/or the second flange 80b surrounds the top surface of the second tray 50b. The first flange 80a extends away from the at least one end of the first tray 50a and/or the second flange 80b extends away from the at least one end of the second tray 50b. The first flange 80a extends perpendicularly away from the at least one end of the first tray 50a or extends perpendicularly away from the top surface of the first tray 80a. The second flange 80b extends perpendicularly away from the at least one end of the second tray 50b or extends perpendicularly away from the top surface of the second tray 50b. The first 80a and second flange 80b being planar, the first 80a and second flange 80b having a top surface 85a, 85b, a width and a length.

Figure 2A:
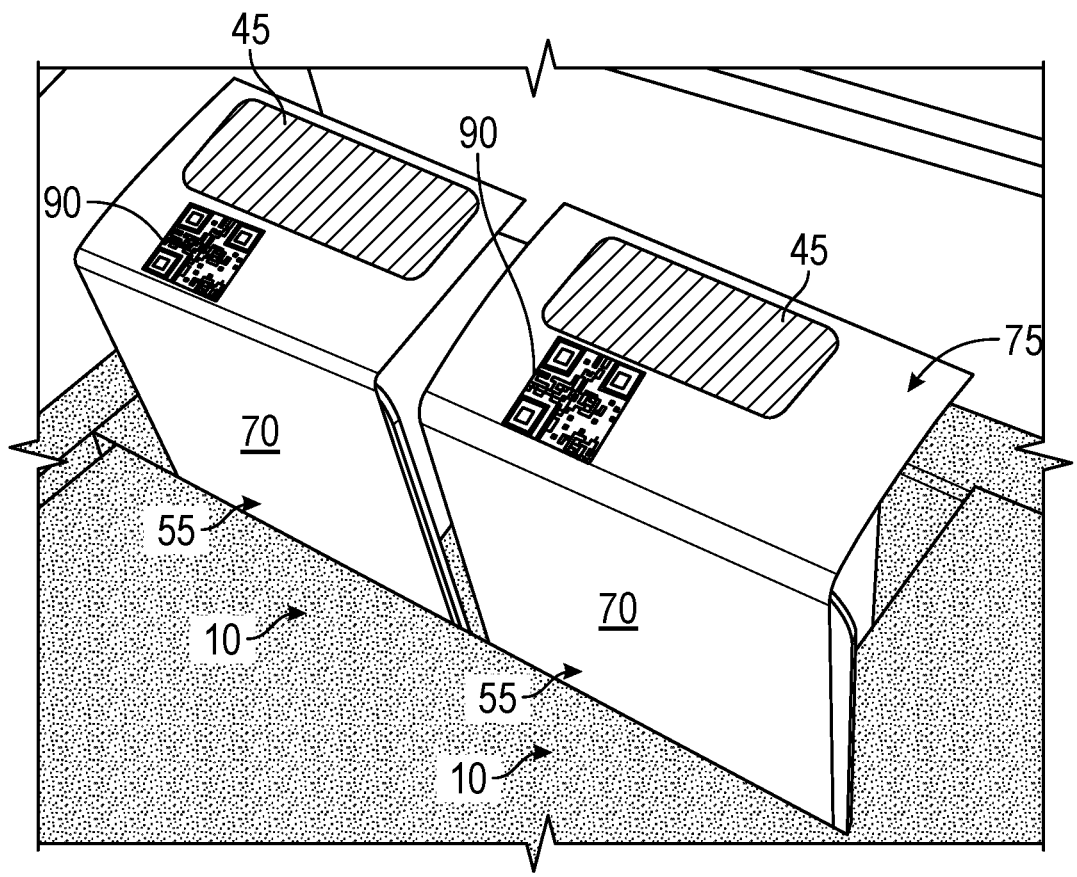
FIGS. 2A-2B depicts an isometric view and a side view of one embodiment of a multi-unit packaging system and a packaging tray assembly.
Figure 2B:
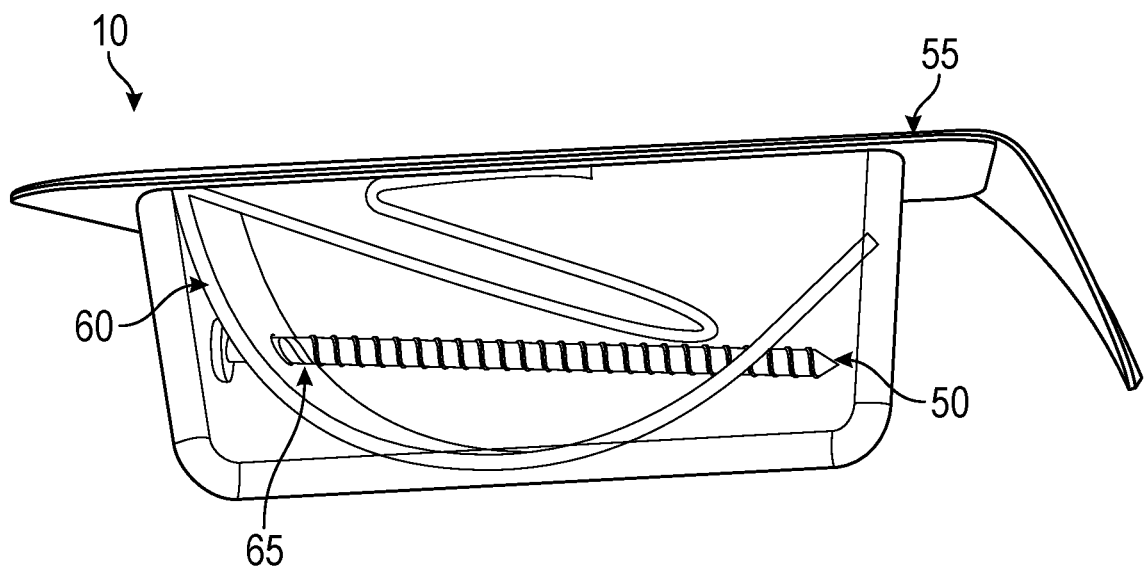

The packaging tray assembly 10, 135, 160, 170 further comprises a barrier 55. The barrier 55 comprises a material. The material comprises any material known in the art to provide a sterile barrier. The barrier 55 is coupled to the at least one tray 50, 50a, 50b by methods known in the art. Such barriers 55 are tested to have a specific barrier peel strength, seal strength or peel force. The barrier 55 having a top surface and a bottom surface. The bottom surface is coupled to the at least one tray 50, 50a, 50b and/or coupled to a top surface 85, 85a, 85b the flange 80, 80a, 80b. The top surface may comprise proper medical device labeling and/or 2D or 3D matrix codes. The barrier 55 may further comprise a first portion 70 and a second portion 75. The first portion 70 is bonded and/or coupled to a top surface 85, 85a, 85b of the flange 80, 80a, 80b and the second portion 75 is free. The first portion 70 comprises a length that is equal to the entire length of the flange 80, 80a, 80b. Accordingly, the first portion 70 comprises a surface area that matches or substantially matches a flange surface area. The barrier 55 covers the inner container 53, 53a, 53b of the at least one tray 50, 50a, 50b. The free end 75 of the barrier 55 extending outwardly and/or downwardly and substantially perpendicular to contact a portion of the flange. At least a portion of the first portion 70 and second portion 75 of the barrier 55 may comprise proper medical device labeling and/or 2D, 3D matrix codes. The barrier 55 further comprising a peel direction. For example, FIGS. 1B and 2A depict one example of the labeling area 45 that may be disposed onto the second portion 75 of the barrier 55.

The packaging tray assembly 10, 135, 160, 170 further comprises a spring-loaded card 60, 145, 175 as shown in FIGS. 3A-3B, 4A-4B, 6, and 9A-9B. The spring-loaded card 60, 145, 175 is sized and configured to be disposed within the at one tray 50, 50a, 50b. The spring-loaded card may match or substantially match the volume, dimensions, length and/or width of the inner container 53, 53a, 53b. Such matching or substantially matching provides a surface friction between the inner container 53, 53a, 53b and a portion of the spring-loaded card 60, 145, 175 to prevent sliding out or migrating out once the spring-loaded card 60, 145, 175 returns to its original configuration after the barrier 55 is peeled from the tray 50, 50a, 50b.

The spring-loaded card 60, 145, 175 further comprising a material. The material comprises an elastic material, a viscoelastic material, a rubber material, a thermoset elastomer material or a thermoplastic elastomer material. The elastic material comprises a fluoroelastomer, resiline chloropene, elastin, nylon, terpene, or neoprine, and/or any combination thereof. The rubber comprises butyl rubber, ethylene propylene rubber (EPR), styrene butadiene rubber (SBR), isoprene rubber, nitrile rubber, silicone rubber, halogenated butyl rubbers, and/or any combination thereof. For example, the spring-loaded card 60, 145, 175 comprises an elastic material. The elastic material properties allow the spring-loaded card 60, 145, 175 to be deformed by a force during coupling of the barrier 55 to the at least one tray 50, 50a, 50b to create a compressed and/or deformed configuration, and when the force is released (e.g., the removal of the barrier 55) the spring-loaded card 60, 145, 175 returns to its original configuration. However, the spring force of the spring-loaded card 60, 145, 175 should not exceed the coupling/peel strength or seal force of the barrier 55 to the at least one tray 50, 50a, 50b to prevent unwarranted or premature detachment and/or penetration. In one embodiment, the spring-loaded card 60, 145, 175 comprises a spring force and the barrier 55 comprises a peel force, the spring force of the spring-loaded card 60, 145, 175 should be less than the peel force or peel strength of the barrier 55.

Figure 3A:
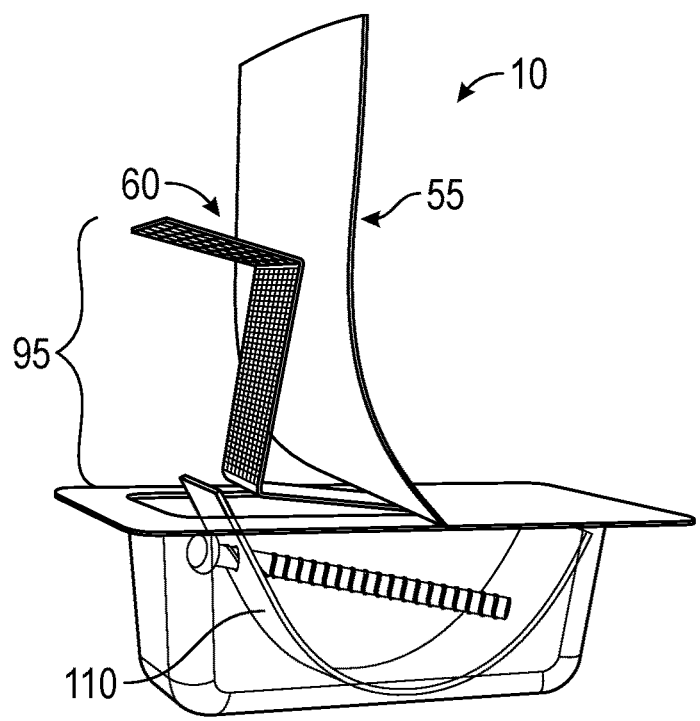
FIGS. 3A-3B depicts an isometric view and a side view of an alternate embodiment of a packaging tray assembly.
Figure 3B:
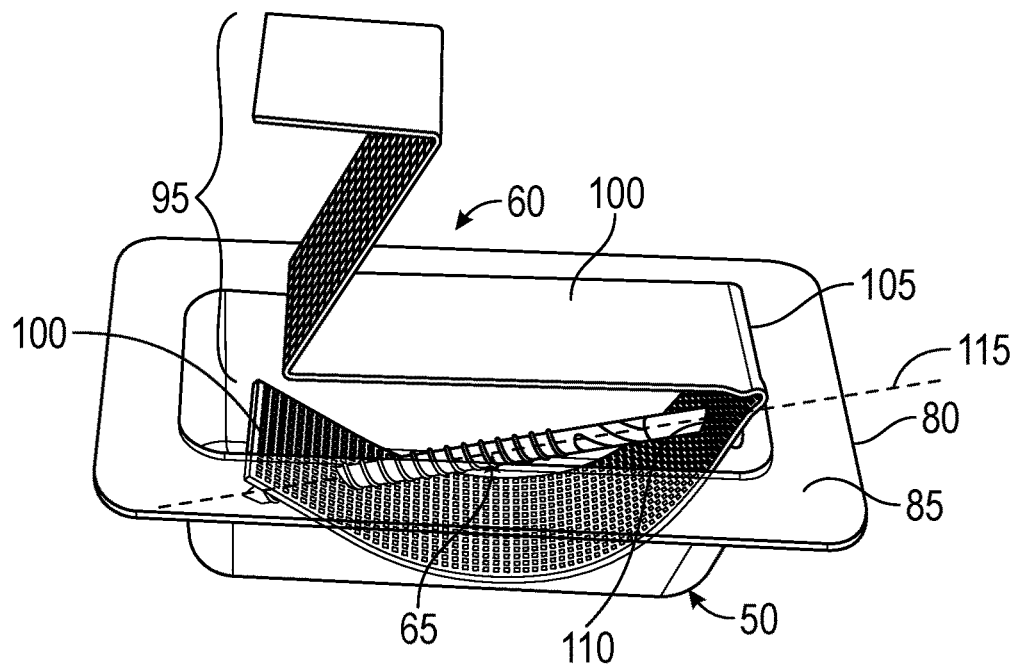
Figure 4A:
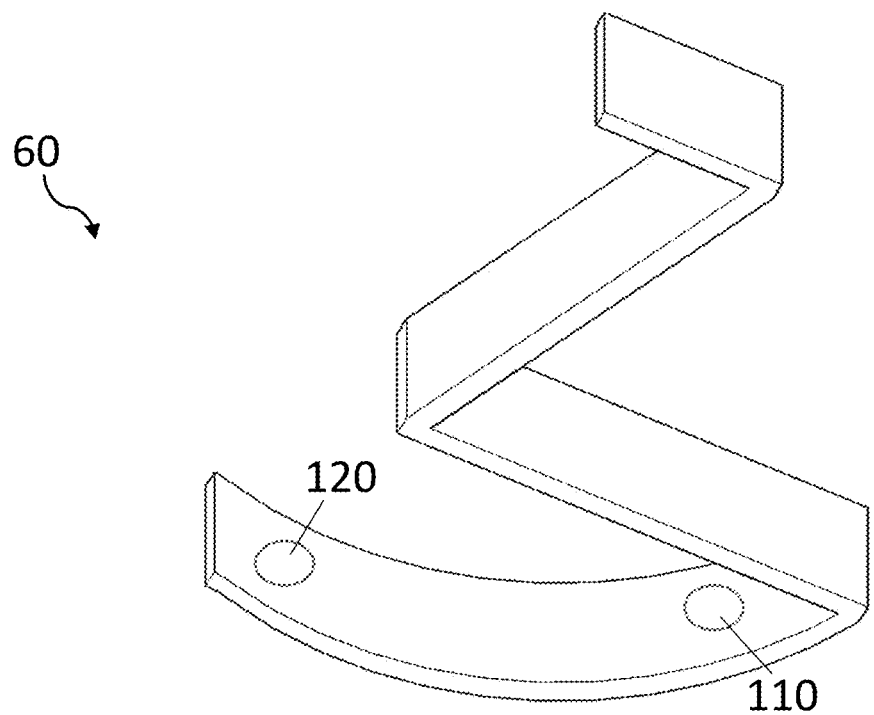
FIGS. 4A-4B depicts different isometric views of one embodiment of a spring loaded card.
Figure 4B:
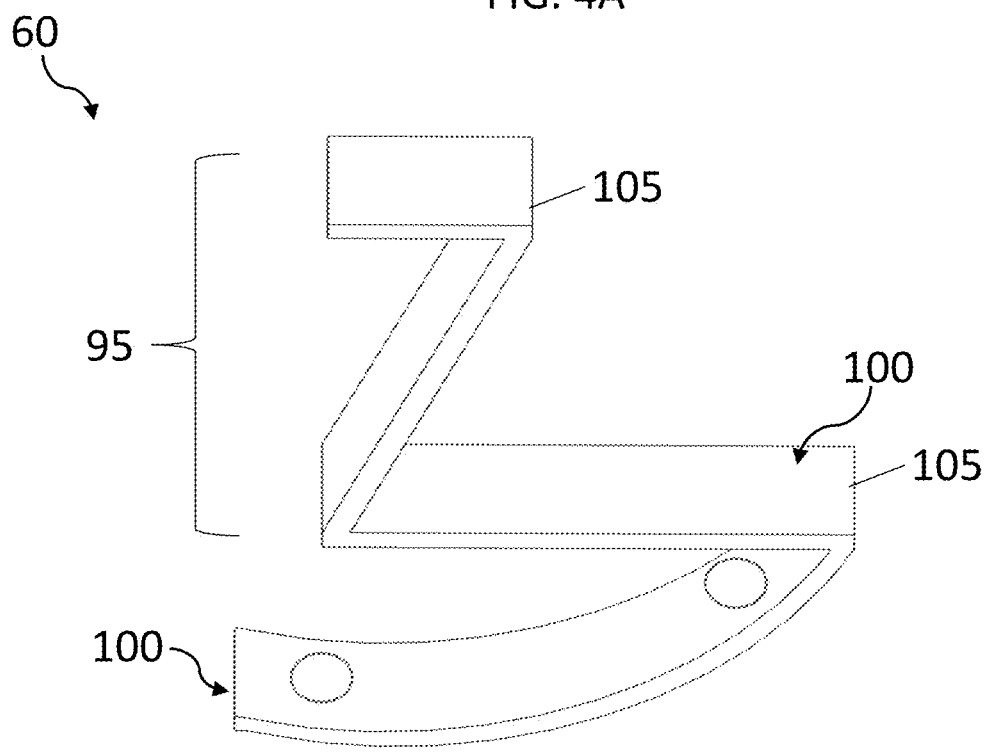
Figures 5A, 5B:
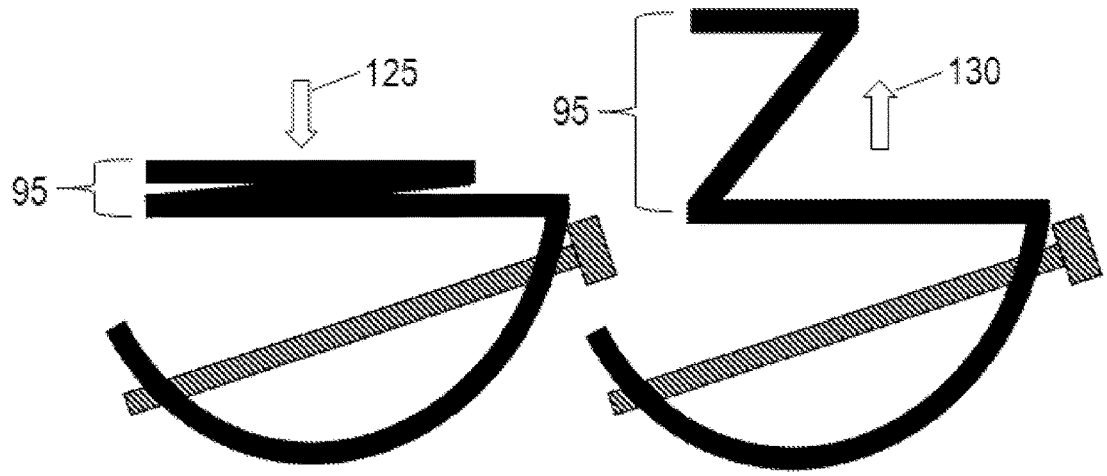
FIGS. 5A-5B depicts side views of the spring-loaded card of FIGS. 4A-4B mechanism of action.

In addition, at least a portion of the spring-loaded card 60, 145, 175 comprises at least one surface having a flat surface or a textured surface as shown in FIG. 3B. Alternatively, at least a portion of the spring-loaded card 60, 145, 175 comprises a at least one surface having a flat surface and a textured surface. Alternatively, the spring-loaded card 60, 145, 157 comprises a first surface and a second surface. The first surface is the same or different than the second surface. The first and/or second surface comprising a flat or textured surface. At least a portion of the first and/or second surface comprising a flat and textured surface. In another embodiment, the spring-loaded card 60, 145, 157 comprises atraumatic edges surrounding the perimeter. The atraumatic edges may include beveled, radiused and/or rounded edges to prevent unwarranted or premature abrasion and/or puncture through the barrier.

The spring-loaded card 60, 145, 175 comprising a body 90 and a leading edge or leading tab 95. In one embodiment, the leading tab 95 extends away from the body 100 of the spring-loaded card 60, 145, 175 as shown in FIGS. 6, 7A-7B, 8A-8B, and 9A-9B. The leading tab 95 extends obliquely way from the body of the spring-loaded card 60, 145, 175. The leading tab 95 having a length, the leading tab length may be equal to and/or less than the length of the inner container 53, 53a, 53b of the at least one tray 50, 50a, 50b. Alternatively, at least one end of the leading tab 95 is coupled to the body 100 of the spring-loaded card 60, 145, 175, and the opposing end is free. The opposing end and/or the free end of the leading tab 95 may be positioned to face the direction during opening the barrier 55 or the peeling of the barrier 55. Should the free end of the leading tab 95 be positioned in the same direction of the peeling of the barrier, at least a portion of the leading 95 may be in contact and/or substantially in contact with the barrier, resulting in a slower release of the spring force or decompression. The opposing end and/or the free end of the leading tab 95 may be positioned in the opposite direction during opening the barrier 55 or the peeling of the barrier 55. Should the free end of the leading tab 95 be positioned in the opposite direction of the peeling of the barrier, at least a portion of the leading 95 may not be in contact with the barrier causing a faster release of the spring force or decompression. Alternatively, the leading edge or tab 95 comprises a first end and a second end. The second end is coupled to the body 100, the first end is free. In another embodiment, at least one end of the leading edge or tab 95 is integral with the body 100 of the spring-loaded card 60, 145, 175. Alternatively, the second end is integral to the body 100 of the spring-loaded card 60, 145, 175.

In another embodiment, the leading tab 95 comprises a first portion, a second portion and at least one fold 105 as shown in FIGS. 10, 2B, 3A-3B, 4A-4B, 5A-5B. The at least one fold 105 is disposed between the first portion and the second portion. The first portion extends away from the second portion. Alternatively, the first portion extends away obliquely from the second portion. In another embodiment, the first portion is planar, and the second portion extends downwardly in an oblique orientation. The second portion is coupled to the body 100 of the spring-loaded card 60, 145, 175.

Figure 6:
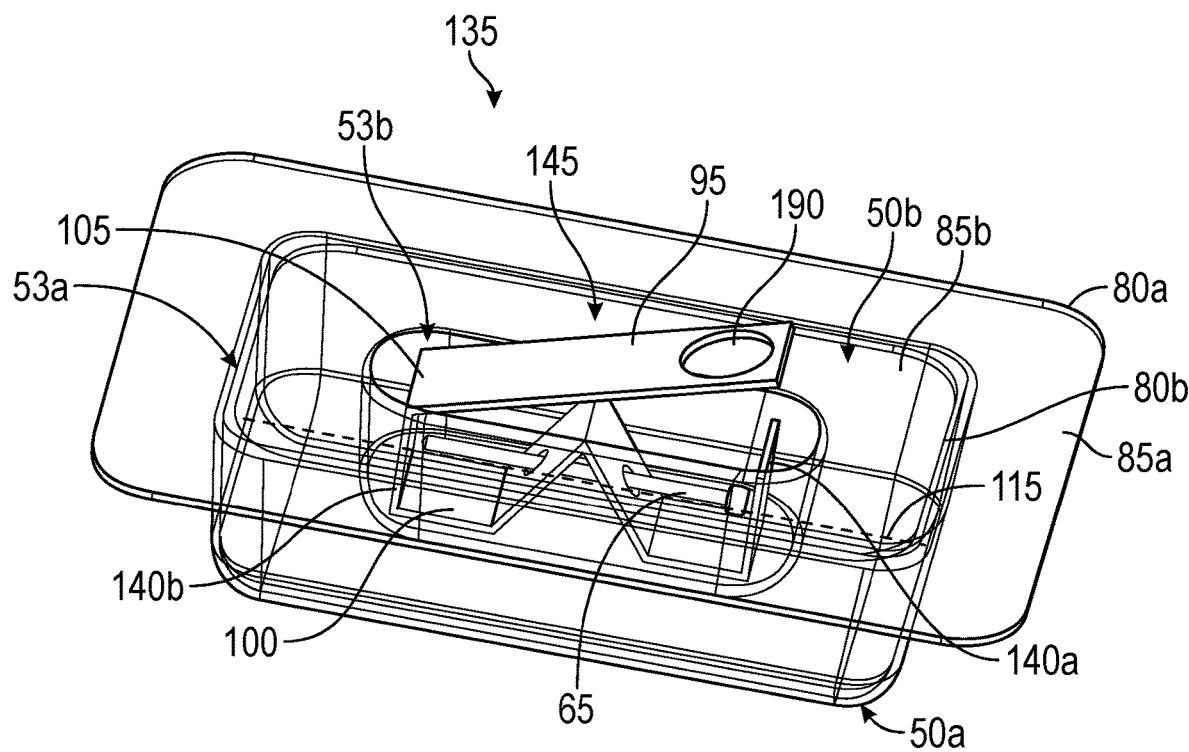
FIG. 6 depicts an isometric view of an alternate embodiment of a packaging tray assembly.
Figure 9A:
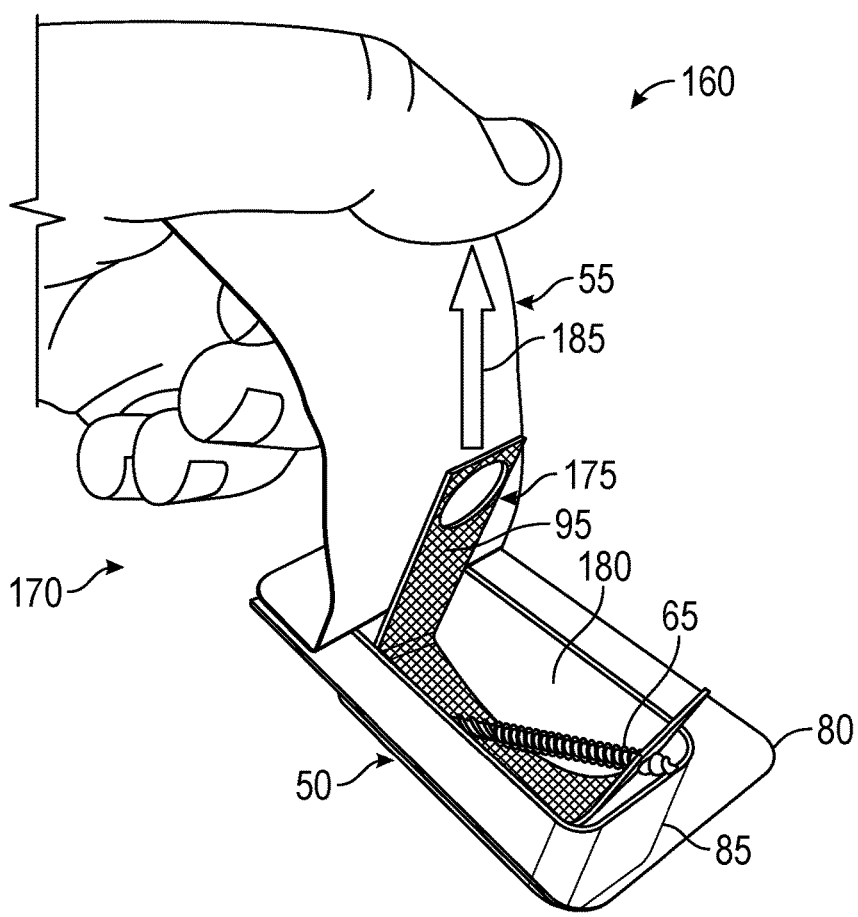
FIGS. 9A-9B depicts isometric views of an alternate embodiment of a packaging tray assembly.
Figure 9B:
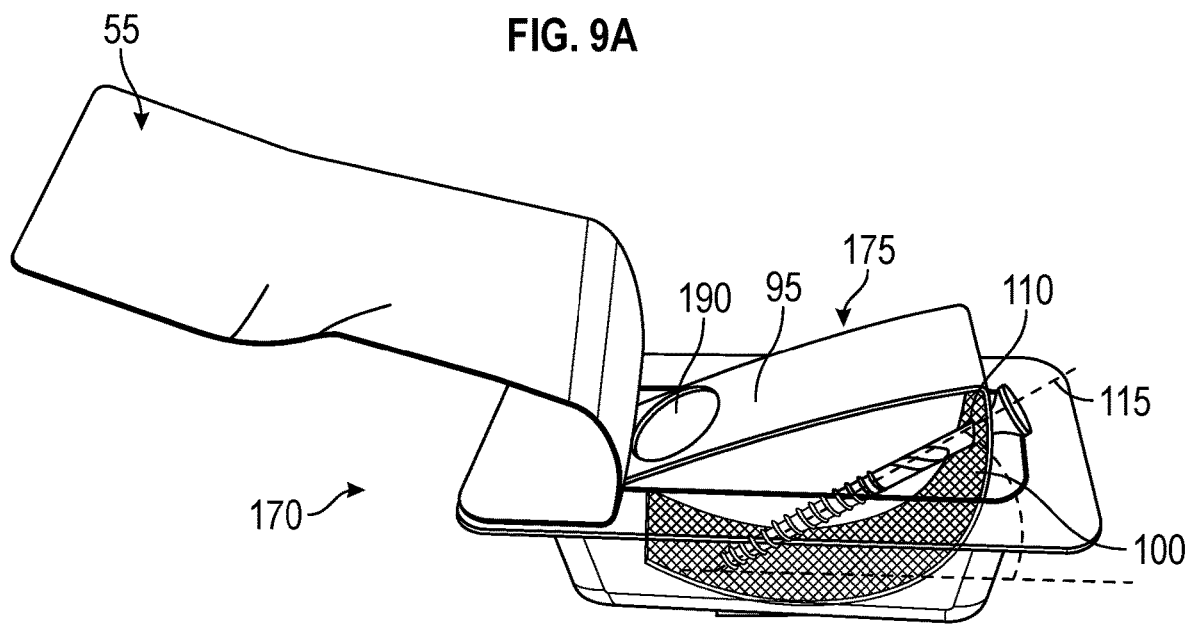
Figure 10A:
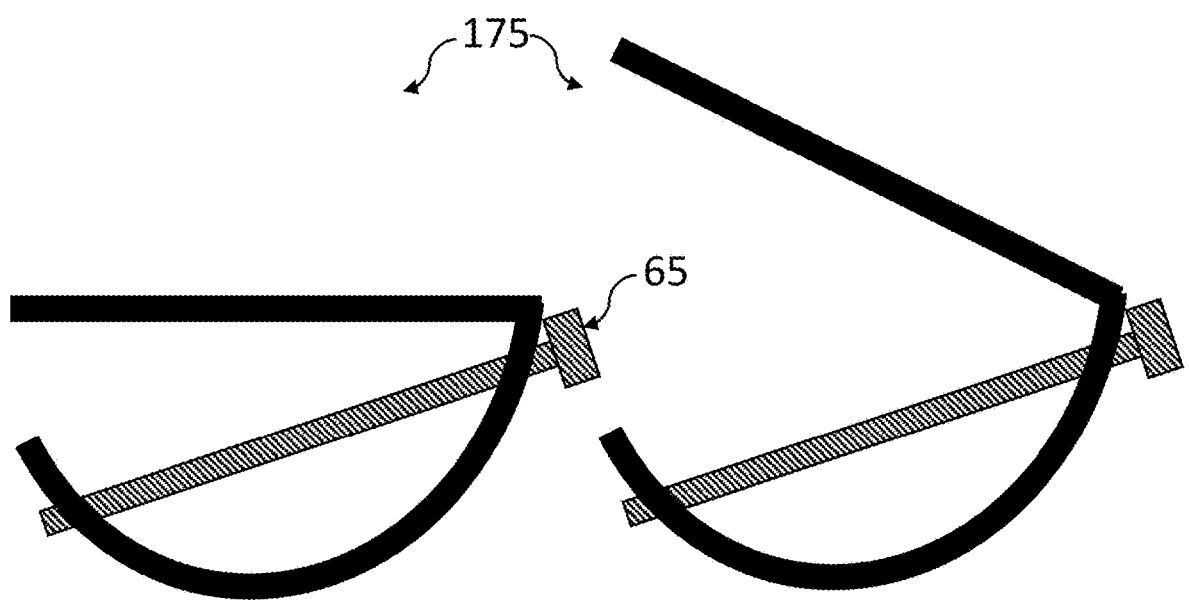
FIGS. 10A-10B depicts side views of the spring-loaded card of FIGS. 9A-9B mechanism of action.
Figure 10B:
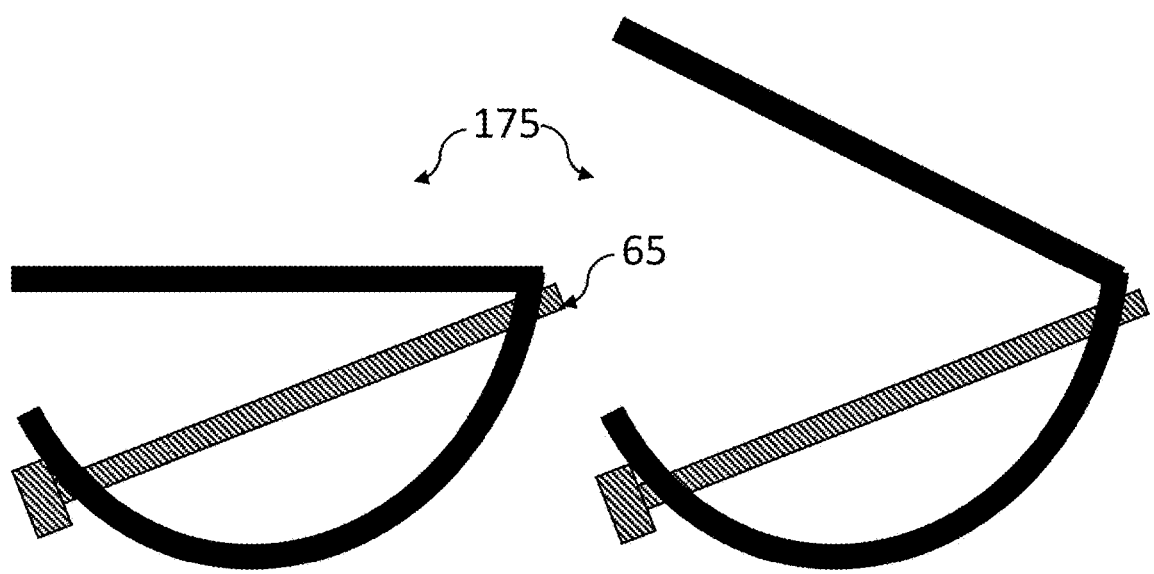

The leading edge or leading tab 95 of the spring-loaded card 60, 145, 175 may further comprise at least one or more openings 190 as shown in FIGS. 6 and 9A-9B. The one or more openings 190 allows easier retrieval of the spring-loaded card 60, 145, 175 by allowing at least one finger to engage, penetrate or pass-through the one or more openings 190. The leading edge or tab 95 may comprise a first end and a second end. The one or more openings 190 may be disposed onto the leading edge or tab 95. The one or more openings 190 may be disposed onto at least one end of the leading edge or tab 95. The one or more openings 190 may be disposed at a first end or second end of the leading edge or tab 95. The one or more openings 190 may be disposed onto a first portion and/or second portion of the leading tab 95. Also, the one or more openings 190 may be sized and configured to receive one or more fingers and/or a surgical tool (e.g., forceps or ratcheted tongs). The one or more openings 190 may also be used as a visual indicator to notify the medical staff or physician where to pick-up or grip the spring-loaded card 60, 145, 175 to retrieve the medical product. The leading edge or tab 95 may further comprise a length. The length may be less than a barrier length to prevent contact from a non-sterile hand of medical staff and/or circulating nurse opening the packaging tray assemblies.

The body 100 of the spring-loaded card 60, 145, 175 comprises one or more openings 110, 120. The one or more openings 110, 120 are sized and configured to receive a portion of the medical product. The one or more openings 110, 120 are spaced apart, and include an angle of orientation 115. The one or more openings 110, 120 are arranged to provide the angle of orientation 115. The angle of orientation 115 allows the medical product to be angled relative to the bottom surface of the at least one tray 50, 50a, 50b and/or inner container 53, 53a, 53b. The angle of orientation 115 may reduce or prevent the medical product from contacting the inner container 53, 53a, 53b and/or provide easier access, transfer and/or removal of the medical product from the spring-loaded card. The angle of orientation 115 may comprise 0 degrees to 60 degrees, 0 degrees to 45 degrees, and/or 0 degrees to 30 degrees, 0 degrees to 15 degrees, 0 degrees to 15 degrees, 5 degrees to 45 degrees, and/or any combination thereof. Alternatively, the angle of orientation 115 may comprise a horizontal or flat orientation and/or the angle of orientation 115 may comprise an oblique orientation. In an alternate embodiment, the one or more openings 110, 120 of the body may match or substantially match a major diameter, minor diameter and/or a shank of a screw. Accordingly, the one or more openings 110, 120 of the body 100 of the spring-loaded card 60, 145, 175 may match or substantially match a width of the medical product. By matching or substantially matching creates a frictional surface to hold the spring-loaded card.

In another embodiment, the body 100 of the spring-loaded card 60, 145, 175 may further comprise a shape. The shape may comprise at least one arch or arch (see FIGS. 10, 2B, 3A-3B, 4A-4B, 5A-5B, 9A-9B, and 10A-10B) and/or at least one undulation (see FIGS. 6, 7A-7B, and 8A-8B). The arch comprises a radius. The arch radius contributes to the spring force of the spring-loaded card 60, 145, 175.

Figure 7A:
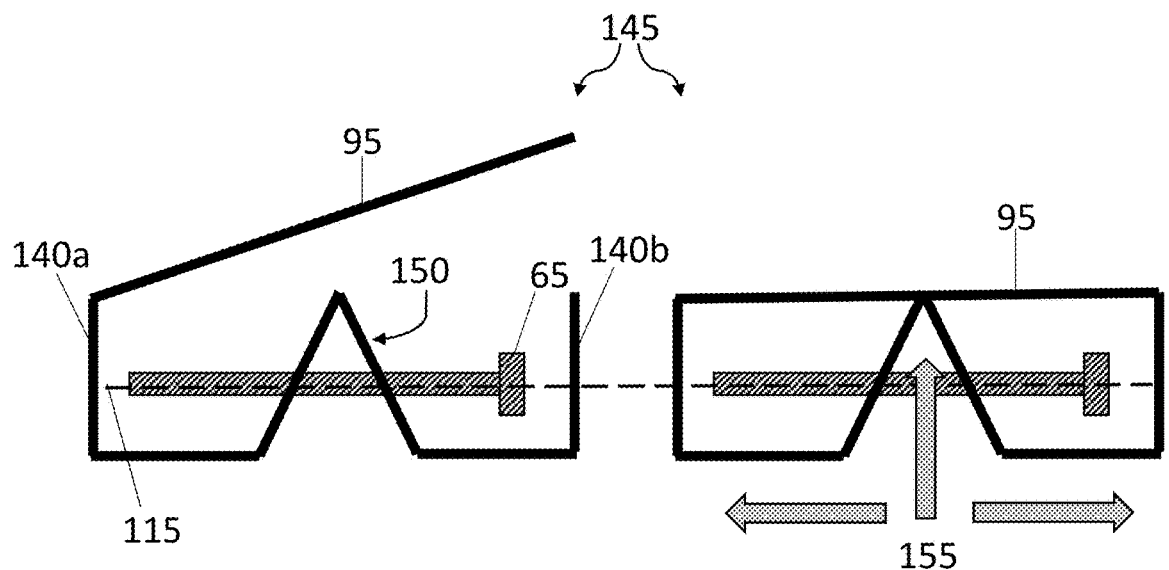
FIGS. 7A-7B depicts side views of the spring-loaded card of FIG. 6 mechanism of action.
Figure 7B:
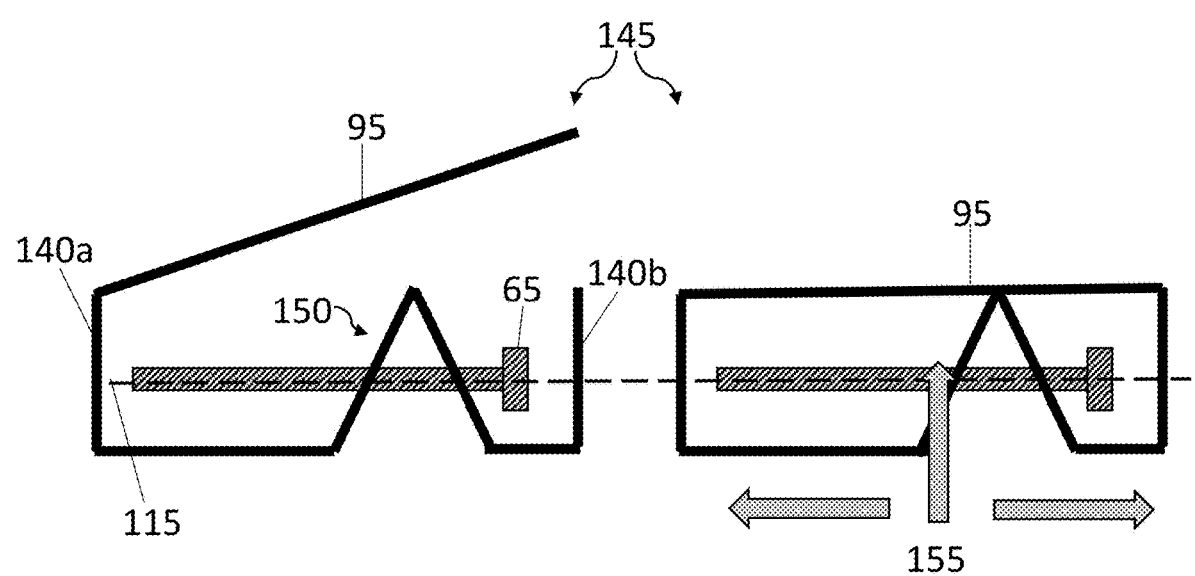
Figure 8A:
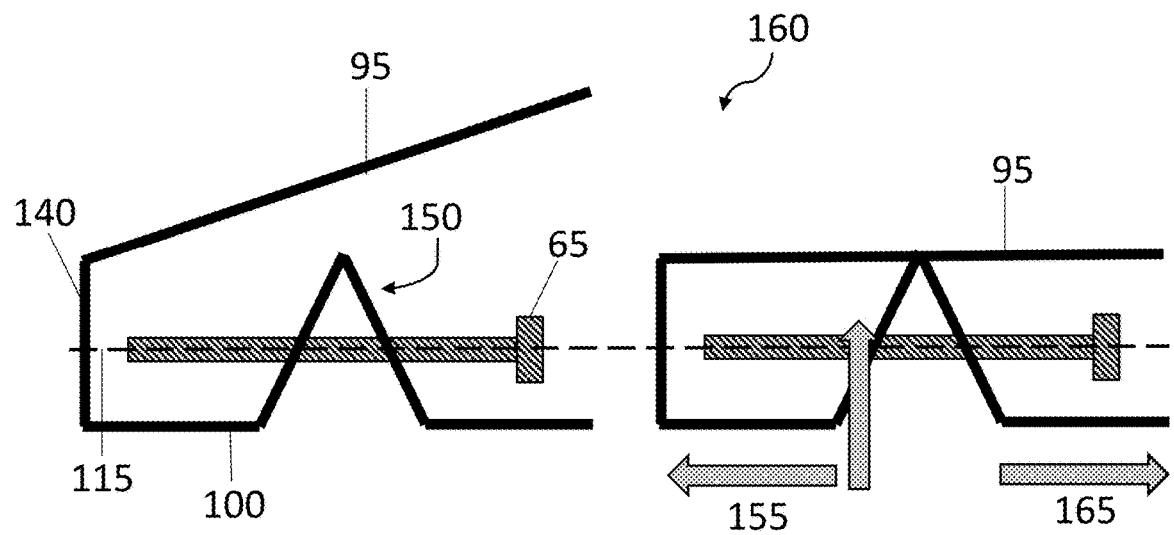
FIGS. 8A-8B depicts side views of an alternate embodiment of a spring-loaded card mechanism of action.
Figure 8B:
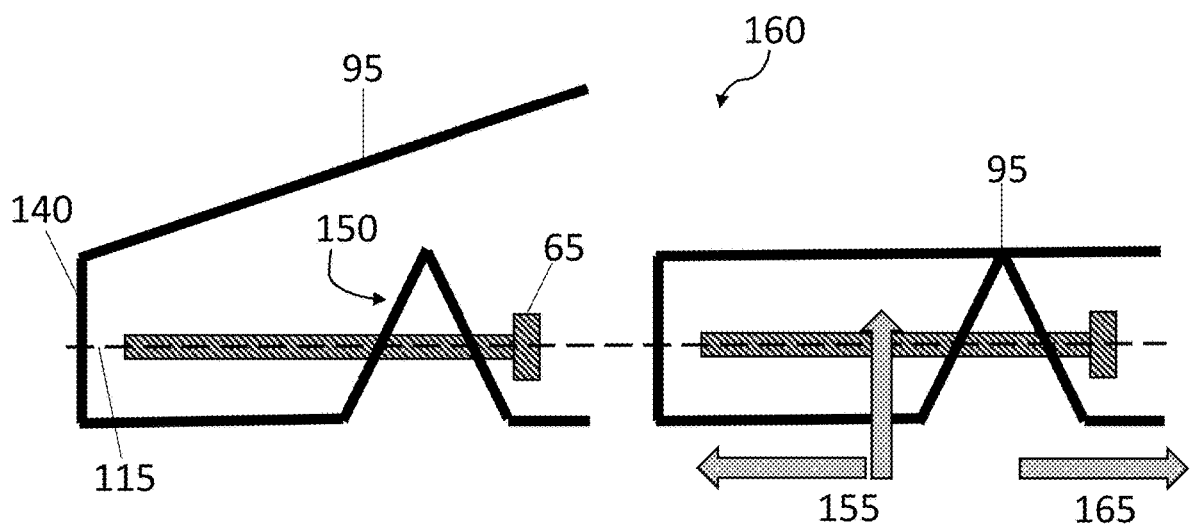

The body 100 of the spring-loaded card 60, 145, 175 may further comprise at least one-fold 105; the body 100 may comprise a plurality of folds 105; the body 100 may comprise two or more folds 105; the body may comprise three or more folds 105; the body may comprise four or more folds 105. A plurality of folds 105 may create at least one undulation 150. The at least one undulation 150 may include smooth or rounded (e.g., similar to sine waves), squared, triangular, or sawtooth shaped undulations. The at least one undulation 150 may comprise a plurality of folds 105 to create the undulated body and/or the undulation. The at least one undulation 150 may be disposed in the center of the body 100 of the spring-loaded card 60, 145, 175 as shown in FIG. 7A. Alternatively, the at least one undulation 150 may be disposed off-center or offset from the center of the body 100 of the spring-loaded card 60, 145, 175. The body 100 of the spring-loaded card 60, 145, 175 may further comprise a first end, a center and a second end. The at least one undulation 150 may be disposed and/or may be positioned between a first wall 140a and/or a second wall 140b. At least a portion of the at least one undulation 150 may be adjacent to a screw head and/or immediately adjacent to a screw head.

In another embodiment, the body 100 of the spring-loaded card 60, 145, 175 may further comprise at least one wall 140, 140a, 140b as shown in FIGS. 6, 7A-7B, and 8A-8B. The at least one wall 140, 140a, 140b that extends upwardly toward the top surface 85, 85a, 85b of the flange 80, 80a, 80b, the first flange 80a and/or the second flange 80b. The body 100 may further comprise at least one wall 140, 140a, 140b that extends perpendicular to a longitudinal axis of the at least one tray 50, 50a, 50b, the first tray 50a and/or the second tray 50b. The body 100 may further comprise at least one wall 140, 140a, 140b that extends perpendicular from a longitudinal axis of the medical product 65. The body 100 may further comprise at least one wall 140, 140a, 140b that extends perpendicular from a bottom surface of the at least one tray 50, 50a, 50b, the first tray 50a and/or the second tray 50b. The at least one wall 140, 140a, 140b may be disposed at least one end of the body 100 of the spring-loaded card 60, 145, 175. Alternatively, the at least one wall 140, 140a, 140b may be disposed at the first end, at the center and/or at the second end of the body 100 of the spring-loaded card 60, 145, 175. The at least one wall 140, 140a, 140b prevents translational movement and/or restricts movement of the medical product 65 in a at least two directions 155.

In another embodiment, the body 100 of the spring-loaded card 60, 145, 175 may further comprise a first wall 140a and a second wall 140b. The first wall 140a and the second wall 140b extends upwardly toward the top surface 85, 85a, 85b of the flange 80, 80a, 80b, the first flange 80a and/or the second flange 80b. The body 100 may further comprise first wall 140a and the second wall 140b that extends perpendicular to a longitudinal axis of the at least one tray 50, 50a, 50b, the first tray 50a and/or the second tray 50b. The body 100 may further comprise first wall 140a and the second wall 140b that extends perpendicular from a longitudinal axis of the medical product 65. The body 100 may further comprise first wall 140a and the second wall 140b that extends perpendicular from a bottom surface of the at least one tray 50, 50a, 50b, the first tray 50a and/or the second tray 50b. The first wall 140a may be disposed at a first end of the body 100 and the second wall 140b may be disposed at the second end of the body 100. The first wall 140a and second walls 140b prevents translational movement and/or restricts of the medical product 65 in two or more directions 155.

Mechanism of Action for Spring Loaded Cards

FIGS. 5A-5B, 7A-7B, 8A-8B and 10A-10B depict alternate embodiments for the mechanism of action of a spring-loaded card 60, 145, 175. The spring-loaded card 60, 145, 175 comprises an original configuration and a compressed configuration. The original configuration and/or original state occurs during the uncompressed or relaxed state, allowing the spring-loaded card 60, 145, 175 to be easily accessed by the medical staff and/or physician. The original configuration comprises one or more folds. The compressed or deformed state or configuration allows the spring-loaded card 60, 145, 175 to deformed to enable the storage of potential energy. Furthermore, during the compressed state and/or configuration, the spring-loaded card 60, 145, 175 provides stability and protection of the medical product 65 within the at least one tray 50, 50a, 50b and can help restrict movement of the medical product 65. The stability and protection are achieved during the compression of the spring-loaded card 60, 145, 175 within the at least one tray 50, 50a, 50b to prevent tumultuous movement and prevent abrasion or puncture of the of the barrier 55. Furthermore, during the compressed state, and/or configuration, the spring-loaded card 60, 145, 175 stored potential energy includes a stored force or spring force. Once the barrier 55 is slowly removed or peeled back, the elasticity or elastic properties of the material and/or the shape of the spring-loaded card 60, 145, 175 contributes to the return of the spring-loaded card to its original configuration by releasing the stored potential energy and/or releasing the stored/spring force so it may be converted to kinetic energy. This kinetic energy forces a portion of the spring-loaded card "pop-up" or extend beyond the top surface 85, 85a, 85b of the flange 80, 80a, 80b of the tray 50, 50a, 50b and/or the top surface of the tray 50, 50a, 50b.

Alternatively, the leading tab 95 of the spring-loaded card 60, 145, 175 may be compressed to store the potential energy. Then, once the barrier 55 is peeled from the at least one tray 50, 50a, 50b, the potential energy is transferred to kinetic energy, forcing the leading edge or tab 95 of the spring-loaded card 60, 145, 175 to extend beyond a top surface 85, 85a, 85b of the flange 80, 80a, 80b and/or the top surface of the tray 50, 50a, 50b. However, the stored force of the spring-loaded card 60, 145, 175 should not exceed the coupling/peel strength or force of the barrier 55 to the at least one tray 50, 50a, 50b to prevent unwarranted or premature detachment and/or penetration.

In one embodiment, a packaging tray assembly 10, 135, 160, 170 comprises a tray 50, 50a, 50b and a spring-loaded card 60, 145, 175. The tray 50, 50a, 50b comprising a flange 80, 80a, 80b and an inner container 53, 53a, 53b. The spring-loaded card 60, 145, 170 being sized and configured to be disposed within the inner container 53, 53a, 53b, the spring-loaded card 60, 145, 175 comprising a body 100 and a leading edge or tab 95, the spring-loaded card 60, 145, 175 being movable from a compressed state that enables the potential energy to be stored to an uncompressed state that enables the potential energy to be released and allowing the leading edge or tab 95 of the spring-loaded card 60, 145, 175 to extend beyond the top surface 85, 85a, 85b of the flange 80, 80a, 80b; and a barrier 55, the barrier 55 being disposed onto the top surface 85, 85a, 85b of the flange 80, 80a, 80b of the tray 50, 50a, 50b. The packaging tray assembly 10, 135, 160, 170 may further comprise a medical product 65.

In another embodiment, a packaging tray assembly 10, 135, 160, 170 comprises a tray 50, 50a, 50b and a spring-loaded card 60, 145, 175. The tray 50, 50a, 50b comprising a flange 80, 80a, 80b and an inner container 53, 53a, 53b. The spring-loaded card 60, 145, 170 being sized and configured to be disposed within the inner container 53, 53a, 53b, the spring-loaded card 60, 145, 175 comprising a body 100 and a leading edge or tab 95, the leading tab 95 being movable from a compressed state that enables the potential energy to be stored to an uncompressed state that enables the potential energy to be released and allowing the leading edge or tab 95 of the spring-loaded card 60, 145, 175 to extend beyond the top surface 85, 85a, 85b of the flange 80, 80a, 80b; and a barrier 55, the barrier 55 being disposed onto the top surface 85, 85a, 85b of the flange 80, 80a, 80b of the tray 50, 50a, 50b. The packaging tray assembly 10, 135, 160, 170 may further comprise a medical product 65.

Accordingly, a portion of the medical product 65 is disposed within spring-loaded card and/or within the body of the spring-loaded card. The medical product 65 having a first end and a second end. The first or second end of the medical product 65 is adjacent to the at least one wall to prevent translational movement and/or restricts movement in at least two directions or a plurality of directions. Alternatively, the first end of the medical product 65 is adjacent to a first wall and a second end is adjacent to a second wall to prevent translational movement and/or restricts movement in at least two or more directions or in at least three or more directions or in a plurality of directions.

Method of Access to Medical Product With Use of Spring-Loaded Card

Figure 11:
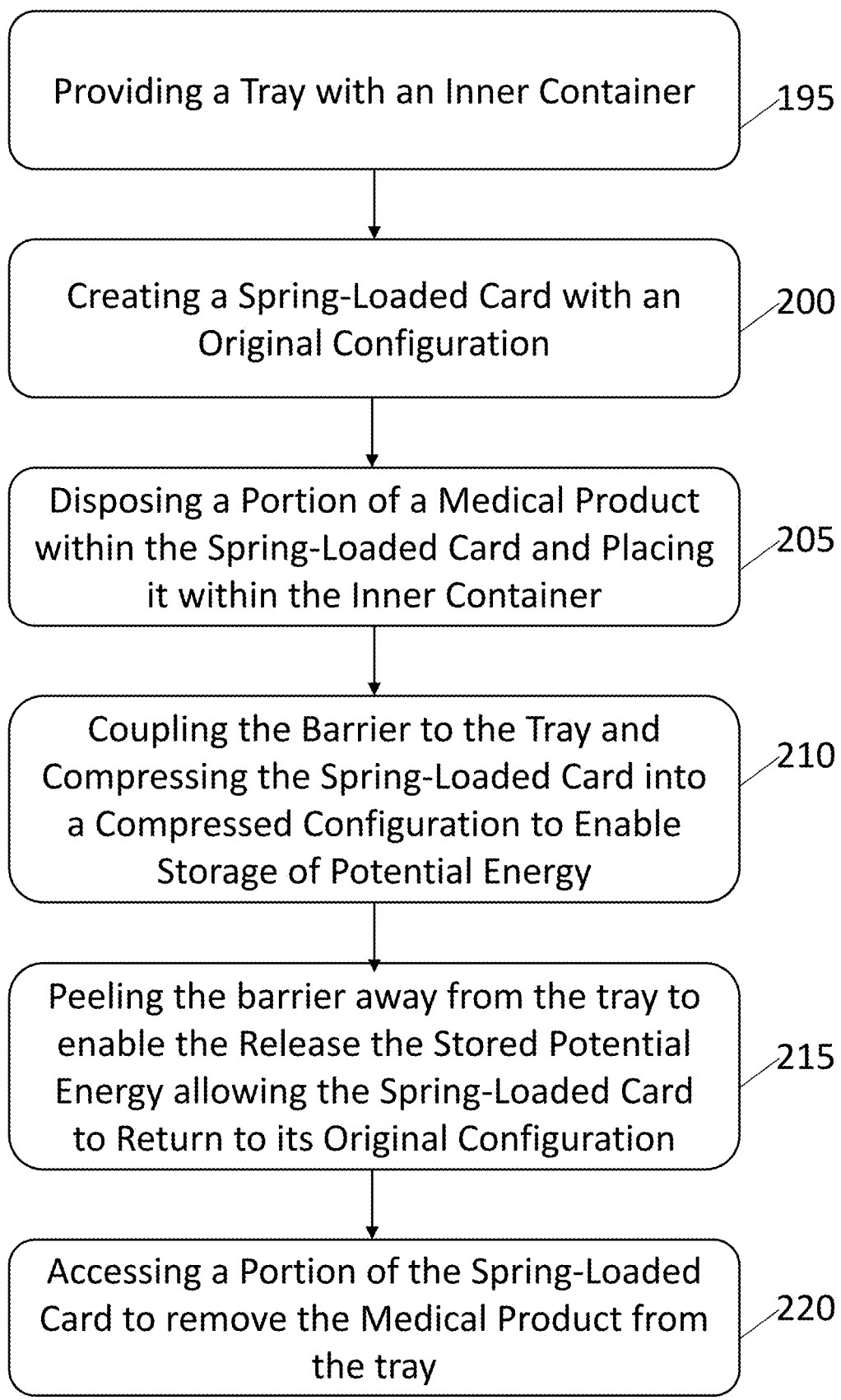
FIG. 11 depicts a flowchart representing one embodiment of a method for easier access to a medical product.

FIG. 11 depicts a flowchart representing one embodiment of a method for easier access to a medical product 65. In one exemplary embodiment, the method of easier access to a medical product 65 comprising the steps of: providing a tray with an inner container and a flange 195; creating a spring-loaded card with an original configuration 200; Disposing a portion of the medical product through the one or more openings of the spring-loaded card and placing it within the inner container of the tray 205; coupling the barrier to the tray and compressing the spring loaded card into a compressed configuration to enable the storage of potential energy 210; Peeling the barrier away from the Tray to enable the release of the stored potential energy and allowing the spring loaded card to return to its original configuration 215; accessing a portion of spring loaded card to remove the medical product from the tray 220.

In another exemplary embodiment, the method of easier access to a medical product 65 comprising the steps of: providing a tray with an inner container and a flange 195; creating a spring-loaded card with an original configuration, the spring-loaded card comprising a body and a leading tab. The body comprising an arch and/or an undulation and one or more openings sized and configured to receive a portion of a medical product. The leading tab comprising at least one opening, the at least one opening sized and configured to receive a portion of an average sized finger and/or a tool. Disposing a portion of the medical product through the one or more openings of the spring-loaded card and placing it within the inner container of the tray 205; coupling the barrier to the tray and compressing the spring loaded card into a compressed configuration to enable the storage of potential energy 210 and a spring force; Peeling the barrier away from the Tray to enable the release of the stored potential energy and allowing the spring loaded card to return to its original configuration 215; accessing the at least one opening on the leading tab of the spring loaded card to remove the medical product from the tray 220.

Example Embodiments

In one embodiment, a multi-unit packaging system comprising: a packaging tray assembly, the packaging tray assembly comprises a tray, a spring-loaded card and a barrier, the spring-loaded card is disposed within the tray, the spring-loaded card comprising a leading edge and a body, at least a portion of the spring-loaded card being movable from a compressed state after the barrier is coupled to a top surface of the tray that enables the potential energy to be stored to an uncompressed state that enables the potential energy to be released after the barrier is removed from the top surface of the tray and the portion of the spring-loaded card to extend beyond the top surface of the tray; and a multi-unit compartment carrier, the multi-unit compartment carrier comprising at least one compartment that is sized and configured to receive the packaging tray assembly. The material comprises an elastic material, a viscoelastic material, a rubber, a thermoset elastomer or a thermoplastic elastomer. The elastic material comprises a fluoroelastomer, resilin chloropene, elastin, nylon, terpene, or neoprene, and/or any combination thereof. The rubber comprises butyl rubber, ethylene propylene rubber (EPR), styrene butadiene rubber (SBR), isoprene rubber, nitrile rubber, silicone rubber, halogenated butyl rubbers, and/or any combination thereof. The leading edge or tab comprising a leading edge or tab length and the barrier comprising a barrier length, the leading edge or tab length is less than the barrier length. The leading edge comprises at least one opening. The body comprises a plurality of openings, the plurality of openings sized and configured to receive a portion of a medical product. Each of the plurality of openings are spaced apart and having an angle of orientation. The angle of orientation comprises a range of 0 degrees to 45 degrees. Alternatively, the angle of orientation comprises a horizontal or oblique orientation.

In another embodiment, a multi-unit packaging system comprising: a packaging tray assembly, the packaging tray assembly comprises a tray, a spring-loaded card and a barrier, the spring-loaded card is disposed within the tray, the spring-loaded card comprising a leading edge and a body, the leading edge being movable from a compressed state after the barrier is coupled to a top surface of the tray that enables the potential energy to be stored to an uncompressed state after the barrier is removed from the top surface of the tray that enables the potential energy to be released and allowing the leading edge of the spring-loaded card to extend beyond the top surface of the tray; and a multi-unit compartment carrier, the multi-unit compartment carrier comprising at least one compartment that is sized and configured to receive the packaging tray assembly. The material comprises an elastic material, a viscoelastic material, a rubber, a thermoset elastomer or a thermoplastic elastomer. The elastic material comprises a fluoroelastomer, resilin chloropene, elastin, nylon, terpene, or neoprene, and/or any combination thereof. The rubber comprises butyl rubber, ethylene propylene rubber (EPR), styrene butadiene rubber (SBR), isoprene rubber, nitrile rubber, silicone rubber, halogenated butyl rubbers, and/or any combination thereof. The leading edge or tab comprising a leading edge or tab length and the barrier comprising a barrier length, the leading edge or tab length is less than the barrier length. The leading edge comprises at least one opening. The body comprises a plurality of openings, the plurality of openings sized and configured to receive a portion of a medical product. Each of the plurality of openings are spaced apart and having an angle of orientation. The angle of orientation comprises a range of 0 degrees to 45 degrees. Alternatively, the angle of orientation comprises a horizontal or oblique orientation.

In another embodiment, a multi-unit packaging system comprising: a packaging tray assembly, the packaging tray assembly comprises a tray, a spring-loaded card and a barrier, the spring-loaded card being sized and configured to be disposed within the tray, the spring-loaded card comprising a body, a leading edge and a material, at least a portion of the spring-loaded card being elastically deformed to a compressed configuration after the barrier is coupled to a top surface of the tray and returned to its original configuration when uncompressed after a barrier is removed from a top surface of the flange; and a multi-unit compartment carrier, the multi-unit compartment carrier comprising at least one compartment that is sized and configured to receive the packaging tray assembly. The material comprises an elastic material, a viscoelastic material, a rubber, a thermoset elastomer or a thermoplastic elastomer. The elastic material comprises a fluoroelastomer, resilin chloropene, elastin, nylon, terpene, or neoprene, and/or any combination thereof. The rubber comprises butyl rubber, ethylene propylene rubber (EPR), styrene butadiene rubber (SBR), isoprene rubber, nitrile rubber, silicone rubber, halogenated butyl rubbers, and/or any combination thereof. The leading edge or tab comprising a leading edge or tab length and the barrier comprising a barrier length, the leading edge or tab length is less than the barrier length. The leading edge comprises at least one opening. The body comprises a plurality of openings, the plurality of openings sized and configured to receive a portion of a medical product. Each of the plurality of openings are spaced apart and having an angle of orientation. The angle of orientation comprises a range of 0 degrees to 45 degrees. Alternatively, the angle of orientation comprises a horizontal or oblique orientation.

In another embodiment, a sterile packaging tray assembly comprising: a tray, the tray comprising an inner container and a flange, the flange surrounds the perimeter of the inner container, the flange having a top surface; and a spring-loaded card, the spring-loaded card being sized and configured to be disposed within the inner container, the spring-loaded card comprising a body and a leading edge, at least a portion of the spring-loaded card being movable from a compressed state after a barrier is coupled to a top surface of the flange that enables the potential energy to be stored to an uncompressed state after the barrier is removed from the top surface of the tray that enables the potential energy to be released and allowing at least a portion of the spring-loaded card to extend beyond the top surface of the flange.

In another embodiment, a sterile packaging tray assembly comprising: a tray, the tray comprising an inner container and a flange, the flange surrounds the perimeter of the inner container, the flange having a top surface; and a spring-loaded card, the spring-loaded card being sized and configured to be disposed within the inner container, the spring-loaded card comprising a body and a leading edge, the leading edge being movable from a compressed state after a barrier is coupled to a top surface of the flange that enables the potential energy to be stored to an uncompressed state after the barrier is removed from the top surface of the flange that enable the potential energy to be released forcing the leading edge of the spring-loaded card to extend beyond the top surface of the flange. The spring-loaded card comprises a material, the material includes an elastic material, a viscoelastic material, a rubber, a thermoset elastomer or a thermoplastic elastomer.

A sterile packaging tray assembly comprising: a tray, the tray comprising an inner container and a flange, the flange surrounds the perimeter of the inner container, the flange having a top surface; and a spring-loaded card, the spring-loaded card being sized and configured to be disposed within the inner container, the spring-loaded card comprising a material, a body and a leading edge, at least a portion of the spring-loaded card or the leading edge being elastically deformed when compressed within the tray after a barrier is disposed on the top surface of the flange to create a compressed configuration and returned to its original configuration when uncompressed after the barrier is removed from the top surface of the flange.

The leading edge comprising a leading edge length and the barrier comprising a barrier length, the leading edge length is less than the barrier length. The leading edge comprises at least one opening.

The body of the spring-loaded card comprises a plurality of openings, the plurality of openings sized and configured to receive a portion of a medical product.

The body of the spring-loaded card comprises a first wall disposed at a first end of the body and a second wall disposed at a second end of the body.

The body of the spring-loaded card comprises a first end, a second end, and at least one undulation disposed between the first end and second end, the at least one undulation including a plurality of openings that are sized and configured to receive a portion of a medical product.

The body of the spring-loaded card comprises: a first end, a second end, and at least one undulation disposed between the first end and second end, the at least one undulation including a plurality of openings that are sized and configured to receive a portion of a medical product; a first wall disposed at a first end; and a second wall disposed at a second end.

The body of the spring-loaded card comprises: a first end, a second end, and at least one undulation disposed between the first end and second end, the at least one undulation including a plurality of openings that are sized and configured to receive a portion of a medical product; a first wall disposed at a first end, the first wall extending upwardly towards the top surface of the flange; and a second wall disposed at a second end, the second wall extending upwardly towards the top surface of the flange.

The material comprises an elastic material, a viscoelastic material, a rubber, a thermoset elastomer or a thermoplastic elastomer. The elastic material comprises a fluoroelastomer, resiline chloropene, elastin, nylon, terpene, or neoprene, and/or any combination thereof. The rubber comprises butyl rubber, ethylene propylene rubber (EPR), styrene butadiene rubber (SBR), isoprene rubber, nitrile rubber, silicone rubber, halogenated butyl rubbers, and/or any combination thereof.

Additional Configuration Considerations

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure. The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosed embodiments are intended to be illustrative, but not limiting, of the scope of the disclosure.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

We claim:

1. A sterile packaging tray assembly comprising:
   a tray, the tray comprising an inner container and a flange, the flange surrounds the perimeter of the inner container, the flange having a top surface;
   a barrier; and
   a spring-loaded card, the spring-loaded card being sized and configured to be disposed within the inner container of the tray, the spring-loaded card comprising a spring force, a material, a first opening and a second opening,
   the first opening and the second opening is sized and configured to receive a portion of a medical product, the first opening is spaced apart from the second opening to create an orientation for the medical product,
   at least a portion of the spring-loaded card being movable from a compressed state after the barrier is coupled to a top surface of the flange that enables the potential energy to be stored to an uncompressed state after the barrier is peeled from the top surface of the tray that enables the potential energy to be released and allowing at least a portion of the spring-loaded card to extend beyond the top surface of the flange.

2. The sterile packaging tray assembly of claim 1, wherein the material of the spring-loaded card comprises an elastic material, a viscoelastic material, a rubber, a thermoset elastomer or a thermoplastic elastomer.

3. The sterile packaging tray assembly of claim 1, wherein the spring-loaded card comprises an arch.

4. The sterile packaging tray assembly of claim 1, wherein the orientation is a horizontal orientation.

5. The sterile packaging tray assembly of claim 1, wherein the orientation is an oblique orientation.

6. The sterile packaging tray assembly of claim 1, wherein the barrier further comprises a seal strength, the spring force of the spring-loaded card is less than the seal strength of the barrier to prevent premature seal failures.

7. A sterile packaging tray assembly comprising:
   a tray, the tray comprising an inner container and a flange, the flange surrounds the perimeter of the inner container, the flange having a top surface;
   a barrier; and
   a spring-loaded card, the spring-loaded card being sized and configured to be disposed within the inner container of the tray, the spring-loaded card comprising a spring force, a material, a body, and a leading tab, the leading tab extends away from the body,
   at least a portion of the spring-loaded card being movable from a first position to a second position, the first position compresses and elastically deforms a portion of the spring-loaded card within the tray after the barrier is sealed to the top surface of the flange and the second position uncompresses the portion of the spring-loaded card after the barrier is peeled away from the top surface of the flange of the tray in a peel direction to allow at least a portion of the spring-loaded card to extend beyond the top surface of the flange of the tray.

8. The sterile packaging tray assembly of claim 7, wherein the material is a thermoset elastomer or a thermoplastic elastomer.

9. The sterile packaging tray assembly of claim 7, wherein the leading tab comprises at least one opening.

10. The sterile packaging tray assembly of claim 7, wherein the body of the spring-loaded card comprises an arch shape, a first opening and a second opening, the first opening and the second opening are sized and configured to receive a portion of a medical product, the first opening is spaced apart from the second opening to create an orientation for the medical product.

11. The sterile packaging tray assembly of claim 10, wherein the orientation is horizontal or oblique.

12. The sterile packaging tray assembly of claim 7, wherein the body of the spring-loaded card comprises a first wall, a second wall, and at least one undulation, the at least one undulation disposed between the first wall and the second wall, the at least one undulation including a plurality of openings that are sized and configured to receive a portion of a medical product, each of the plurality of openings are spaced apart to create an orientation of the medical product.

13. The sterile packaging tray assembly of claim 12, wherein the orientation is horizontal or oblique.

14. The sterile packaging tray assembly of claim 7, wherein the barrier further comprises a seal strength, the spring force of the spring-loaded card is less than the seal strength of the barrier to prevent premature seal failures.

15. The sterile packaging tray assembly of claim 7, wherein the at least a portion of the spring-loaded card comprises a portion of the leading tab.

16. The sterile packaging tray assembly of claim 7, wherein the leading lab further comprises a free end, the free end is positioned facing the same direction as the peeling direction.

17. The method of easier access to a medical product comprising the steps of:
   Providing a tray with an inner container and a flange, the flange surrounding the perimeter of the inner container, the flange having a top surface;
   Creating a spring-loaded card with an original configuration, the spring-loaded card comprising a material, a body and a leading edge;

Disposing a portion of a medical product within a portion of the spring-loaded card and placing the spring-loaded card with the original configuration within the inner container of the tray;

Compressing at least a portion of the spring-loaded card within the inner container by sealing a barrier to the top surface of the flange to create a compressed configuration to enable the storage of potential energy;

Peeling the barrier away from the top surface of the flange in a peel direction to enable the release of stored potential energy allowing the spring-loaded card to return to its original configuration and having the portion of the spring-loaded card extending beyond the top surface of the flange of the tray; and Accessing a portion of the spring-loaded card that extends beyond the top surface of the flange for easier access and removal of the medical product.

18. The method of easier access to a medical product of claim 17, the material comprising a thermoset elastomer or a thermoplastic elastomer.

19. The method of easier access to a medical product of claim 17, the body of the spring-loaded card comprises an arch shape, a first opening and a second opening, the first opening and the second opening are sized and configured to receive a portion of a medical product, the first opening is spaced apart from the second opening to create an oblique orientation for the medical product.

20. The method of easier access to a medical product of claim 17, wherein the leading lab further comprises a free end, the free end is positioned facing the same direction as the peeling direction.

* * * * *